(12) United States Patent
Rajakumar et al.

(10) Patent No.: US 7,902,421 B2
(45) Date of Patent: Mar. 8, 2011

(54) ANIMAL MODEL FOR SCHIZOPHRENIA

(75) Inventors: Nagalingam Rajakumar, London (CA); Bavani Rajakumar, London (CA)

(73) Assignee: London Health Sciences Centre Research Inc., London, Ontario (CA)

( * ) Notice: Subject to any disclaimer, the term of this patent is extended or adjusted under 35 U.S.C. 154(b) by 16 days.

(21) Appl. No.: 10/547,346

(22) PCT Filed: Mar. 1, 2004

(86) PCT No.: PCT/CA2004/000304

§ 371 (c)(1),
(2), (4) Date: Oct. 30, 2006

(87) PCT Pub. No.: WO2004/087217

PCT Pub. Date: Oct. 14, 2004

(65) Prior Publication Data

US 2007/0079390 A1    Apr. 5, 2007

Related U.S. Application Data

(60) Provisional application No. 60/450,684, filed on Mar. 3, 2003.

(51) Int. Cl.
*A01K 67/00*    (2006.01)
*A01K 67/033*   (2006.01)
*G01N 33/00*    (2006.01)
*C12N 15/00*    (2006.01)

(52) U.S. Cl. .................. 800/9; 800/3; 800/21
(58) Field of Classification Search ............ 800/9, 800/3, 21
See application file for complete search history.

(56) References Cited

U.S. PATENT DOCUMENTS 5,549,884 A    8/1996  Weinberger et al.

FOREIGN PATENT DOCUMENTS

WO    WO 00/11943    3/2000

OTHER PUBLICATIONS

Bunney et al., Evidence for a compromised dorsolateral prefrontal cortical parallel circuit in schizophrenia, Brain Res Brain Res Rev. 31(2-3):138-46, 2000.*
Eastwood et al., Interstitial white matter neuron density in the dorsolateral prefrontal cortex and parahippocampal gyrus in schizophrenia. Schizophr Res. 79(2-3):181-8, 2005.*
Matthaei, Genetically manipulated mice: a powerful tool with unsuspected caveats. J Physiol. 582(Pt 2):481-8, 2007.*
Saunders et al., Origin and fate of fetuin-containing neurons in the developing neocortex of the fetal sheep, Anat Embryol (Berl). 186(5):477-86, 1992.*
Clapcote et al., Behavioral phenotypes of Disc1 missense mutations in mice, Neuron 54(3):387-402, 2007.*
Low et al., What is a schizophrenic mouse? Neuron, 54(3):348-9, 2007.*
Rioux et al., Distribution of microtubule-associated protein MAP2-immunoreactive interstitial neurons in the parahippocampal white matter in subjects with schizophrenia, Am J Psychiatry 160:149-153, 2003.*
Lazar et al., Injections of NGF into neonatal frontal cortex decrease social interaction as adults: a rat model of schizophrenia, Schizophr Bull. 34(1):127-36, 2008.*
Akil, M. et al., "Lamins-Specific alterations in the dopamine innervation of the prefrontal cortex in schizophrenic subjects", *American Journal of Psychiatry*, (1999), 156, pp. 1580-1589.
Allendoerfer, K.L. et al., "The Subplate, a transient neocortical Structure: It's role in the development of connections between Thalamus and Cortex", *Annual Review of Neuroscience*, (1994), vol. 17, pp. 185-218.
Aloe, L. et al., "Studies in Animal Models and Humans Suggesting a Role of Nerve Growth Factor in Schizophrenia-like Disorders" *Behavioral Pharmacology*, (2000), vol. 11 (3-4), pp. 235-242.
Anderson, S.A., "Increased Density of Microtubule associated protein 2-immunoreactive neurons in the prefrontal white matter of schizophrenic subjects", *Schizophrenia Research*, (1996), vol. 19, pp. 111-119.
Bunney, Blynn Garland et al., "Neuropathological studies of brain tissue in schizophrenia", Journal of Psychiatric Research, (1997), vol. 31(2), pp. 159-173.
Chua, S.E. et al., "Schizophrenia—a brain disease? A critical review of structural and functional cerebal abnormality in the disorder", *British Journal of Psychiatry*, (1995), vol. 166, pp. 563-582.
Frade, JM et al., "Induction of cell death by endogenous nerve growth factor through its p75NTR receptor", Natture, (1996), vol. 383, pp. 166-168.
Friedman, W.J. et al., "Neurotrophin signaling via Trks and p75", *Experimental Cell Research*, (1999), vol. 253, pp. 131-142.
Ghosh, A., "Subplate neurons and the patterning of thalamocortical connections", *Ciba Foundation Symposium*, (1995), vol. 193, pp. 150-172.
Harrison, P.J., "The neuropathology of schizophrenia—A critical review of the data and their interpretation", *Brain*, (1999), vol. 122, pp. 593-624.
Johnson, D., et al., "Expression and structure of the human NGF receptor", *Cell*, (1986), vol. 47(4), pp. 545-554.
Kokkinidis, L. et al., "Amphetamine models of paranoid schizophrenia: an overview and elaboration of animal experimentation", *Psychological Bulletin*, (1980), vol. 88, pp. 551-579.
Lee, F.S. et al., "The uniqueness of being a neutrophin receptor", *Current Opinion in Neurobiology*, (2001), vol. 11, pp. 281-286.
Lewis DA. Levitt P. et al., "Schizophrenia as a disorder of neurodevelopment", *Annual Review of Neuroscience*, (2002), vol. 25, pp. 409-432.

(Continued)

Primary Examiner — Wu-Cheng Winston Shen
(74) Attorney, Agent, or Firm — Sim & McBurney

(57) ABSTRACT

The invention is an animal model which exhibits neuropathological and behavioral features associated with human schizophrenia. The invention also encompasses an in vivo method of preparing an animal model of human schizophrenia. Such a model is useful for screening and identifying therapeutic agents for treating human schizophrenia.

22 Claims, 8 Drawing Sheets

OTHER PUBLICATIONS

Lipska, B.K. et al., "Postpubertal emergence of hyperresponsiveness to stress and to amphetamine after neonatel excitotoxic hippocampal damage: a potential animal model of schizophrenia", *Neuropsychopharmacology*, (1993), vol. 9, pp. 67-75.

Lipska, B.K.et al., "Effects of reversible inactivation of the neonatal ventral hippocampus on behaviour in the adult rat", *Journal of Neuroscience*, (2002), vol. 22(7), pp. 2835-2842.

Marenco, S. et al., The neurodevelopmental hypothesis of schizophrenia: following a trail of evidence from cradle to grave, *Developmental Psychopathology*, (2000), vol. 12(3), pp. 501-527.

McQuillen Patrick S et al. "Selective vulnerability of subplate neurons after early neonatal hypoxia-ischemia", *Journal of Neuroscience*, (2003), vol. 23(8), pp. 3308-3315.

Nachman, R.J. et al., "Pseudodipeptide analogs of the pyrokinin/PBAN (FXPRLa) insect neuropeptide family containing carbocyclic Pro-mimetic conformational components", *Regulatory Peptides*, (1995), vol. 57(3), pp. 359-370.

Rajakumar B et al. "Ontogeny of schizophrenia: lessons from a novel animal model", *Society for Neuroscience Abstract Viewer and Itinerary Planner* (2003) Abstract No. 774.13.

Rajakumar, N. et al., "Effects of intrastriatal infusion of D2 receptor antisense oligonucleotide on apomorphine-induced behaviors in the rat", *Synapse*, (1997), vol. 26(3), pp. 199-208.

Rajakumar N et al., "Altered neurotrophin receptor function in the developing prefrontal cortex leads to adult-onset dopaminergic hyperresponsivity and impaired prepulse inhibition of acoustic startle", *Biological Psychiatry*, (2004), vol. 55(8), pp. 797-803.

Rajakumar, N., "Nerve growth factor causes apoptosis of subplate cells in developing cerebral cortex via p75 dependent mechanism", *Society for Neuroscience Abstract Viewer and Itinerary Planner* (2002) Abstract No. 426. 16.

Rajakumar, N. et al., "Parvalbumin-containing GABAergic neurons in the basal ganglia output system of the rat", *Journal of Comparative Neurology*, (1994), vol. 350(2), pp. 324-336.

Roux, P. P. et al., "Neurotrophin signaling through the p75 neurotrophin receptor", *Progress in Neurobiology*, (2002), vol. 67, pp. 203-233.

Super, H. et al., "The functions of the preplate in development and evolution of the neocortex and hippocampus", *Brain Research Reviews*, (1998), vol. 27, pp. 40-64.

Thome J et al., "Neurotrophic factors and the maldevelopment hypothesis of schizophrenic psychoses", *Journal of Neural Transmission*, (1998), vol. 105(1), pp. 85-100.

Uehara, T. et al., "Neonatal lesions of the left entorhinal cortex affect dopamine metabolism in the rat brain", *Brain Research*, (2000), vol. 860, pp. 77-86.

Volk D. et al., "GABA transporter-1 mRNA in the prefrontal cortex in schizophrenia: decreased expression in a subset of neurons", *American Journal of Psychiatry*, (2001), vol. 158(2), pp. 256-265.

Wang Cheng et al., "Blockade of phencyclidine-induced cortical apoptosis and deficits in prepulse inibition by M40403, a superoxide dismutase mimetic", *Journal of Pharmacology and Experimental Therapeutics*, (2003), vol. 304(1), pp. 266-271.

Woo, T.U. et al., "A subclass of prefrontal gamma-aminobutyric acid axon terminals are selectively altered in schizophrenia", *Proceedings of the National Academy of Science* U.S.A., (1998), vol. 95(9), pp. 5341-5346.

\* cited by examiner

Control NGF

\* Lateral ventricle

ANIMAL MODEL FOR SCHIZOPHRENIA

FIELD OF THE INVENTION

The present Invention relates to an animal model which exhibits neuropathological and behavioral features associated with human schizophrenia. More specifically, the invention is an in vivo method of preparing an animal model of human schizophrenia. Such a model is useful for screening and identifying potential therapeutic agents in the treatment of schizophrenic symptoms in humans.

BACKGROUND OF THE INVENTION

Throughout this application, various references are cited in parentheses to describe more fully the state of the art to which this invention pertains. The disclosure of these references is hereby incorporated by reference in their entirety into the present-disclosure.

Schizophrenia can be broadly defined as any of a group of psychotic disorders usually characterized by withdrawal from reality, illogical patterns of thinking, delusions, and hallucinations, and accompanied in varying degrees by other emotional, behavioral, or intellectual disturbances. In addition to the behavioral abnormalities, several post-mortem and in-vivo imaging studies of schizophrenic brains have described a number of structural defects, including loss of nerve fibers and synaptic markers, a reduced size and number of nerve cells, aberrant distribution of nerve cells, and ventricular enlargement (Volk, Austin, Pierri Sampson and Lewis, American Journal of Psychiatry 2001, 158: 256-265: Woo, Whitehead, Melchitzky and Lewis, Proceedings of the National Academy of Science U.S.A. 1998, 95: 5341-5346; Chua and McKenna. British Journal of Psychiatry 1995, 166: 563-582; Lewis and Levitt, Annual Review of Neuroscience 2002, 25:409-432; Harrison, P. J. 1999, Brain 122; 593-624).

Schizophrenia is associated with dopamine imbalances in the brain. It is believed that schizophrenia may be caused by genetic, other biological, and psychosocial factors. A number of epidemiological, postmortem and in-vivo imaging studies have indicated that early developmental injury and consequent defective cerebral cortical organization may underlie the adult manifestation of schizophrenic symptoms (Chua and McKenna, British Journal of Psychiatry 1995,166: 563-582; Marenco and Weinberger, Developmental Psychopathology 2000, 12: 501-527).

While animal models have been developed to represent some features of schizophrenia, none have shown any structural neuropathological features similar to those described in post-mortem brains of schizophrenic patients (Kokkinidis and Anisman, Psychological Bulletin 1980, 88: 551-579; Lipska, Jaskiw and Weinberger, Neuropsychopharmacology 1993, 9: 67-75; Uehara, Tanii, Sumlyoshi and Kurachi, Brain Research 2000, 860: 77-86).

U.S. Pat. No. 6,549,884 discloses an animal model exhibiting certain behaviors associated with human schizophrenia. A neurotoxin is used to induce neonatal lesions of the ventral hippocampus in animals that have not yet reached puberty (Lipska, Jaskiw and Weinberger, Neuropsychopharmacology 1993, 9: 67-75). This model is limited in that only behavioral abnormalities consistent with enhanced mesolimbic dopamine hyper-responsivity to environmental stress or pharmacological challenge are manifested in post-pubertal life. This model does not show any structural changes described in post-mortem or in-vivo examinations of schizophrenic brains. Furthermore, the lesion inflicted bilaterally in the ventral hippocampus in the prepubescent animal persists in adulthood as large, permanent structural damage to the ventral hippocampal area therefore precluding behavioral and cognitive testing involving intact hippocampal circuitry.

Recently, a modified method of neonatal ventral hippocampal lesioning has been described (Lipska Halim, Segal and Weinberger, Journal of Neuroscience 2002, 22: 2835-2842). This method produces animals showing certain behavioral features of enhanced post-pubertal emergence of dopamine hyper-responsitivity with apparently normal ventral hippocampus Nevertheless, the resultant animals do not show any neuropathological abnormalities of schizophrenia.

Presently, none of the animal models used in schizophrenia research show any neuropathological features of the disease. It would therefore be beneficial to provide a schizophrenia animal model that overcomes the limitations of currently used models. More specifically, it would be useful to establish an animal model of schizophrenia that exhibits neuropathological and behavioral features of human schizophrenia with apparently intact thalamic, hippocampal, cortical and subcortical circuits similar to that seen In schizophrenic patients. A desirable animal model would exhibit both neuropathological and behavioral features closely resembling the disease in humans and prove useful for the identification of pharmaceutical compounds for their potential antipsychotic property and effects on cognitive function. Such a model could also be employed in studies to determine the mechanisms underlying the manifestation of behavioral and cognitive symptoms of schizophrenia and to Identify potential molecular targets to treat schizophrenic symptoms.

SUMMARY OF THE INVENTION

The present invention is an animal model of schizophrenia. The invention also encompasses a new method for making an animal model of schizophrenia.

The animal model of the invention exhibit neuropathological and behavioral features of schizophrenia with apparently intact thalamic, hippocampal, cortical and subcortical circuits as seen in human schizophrenic patients. The animal model of the inventionexhibits behavioral changes indicating enhanced subcortical dopamine responsivity manifested only in post-pubertal animals; diminished GABA transporter-1 immunoreactive synapses in the prefrontal cortex; altered laminar distribution as well as loss of GABAergic terminals in the prefrontal cortex; decreased density of dopamine fibers in the lower layers of the prefrontal cortex; and moderately enlarged lateral and third ventricles. These neuropathological changes are frequently observed in postmortem studies in human schizophrenic brains.

The schizophrenia animal model of the present invention is made by a method comprising the premature elimination of subplate cells in the developing prefrontal cerebral cortex in an animal. The subplate cells are eliminated during a "critical period" which is defined as the time period when thalamic and dopaminergic fibers begin to invade the developing prefrontal cortex. This critical period lasts until the subplate cells of the developing prefrontal cerebral cortex die. During this critical period, subplate cells express the p75 receptor (the nerve growth factor receptor) but do not express the trkA receptor (another neurotrophin nerve growth factor receptor). The elimination of subplate cells during such a critical period leads to neuropathological and behavioral features of human schizophrenia.

In one aspect of the invention, subplate cells of the prefrontal cortex are eliminated by the administration of an agent that kills or suppresses the function of these cells. The agent is administered in an amount and time to essentially kill or suppress the function of the subplate cells of the developing prefrontal cortex during the critical period established for the animal, in one embodiment, this is accomplished by the intracerebral administration of nerve growth factor into the subplate cells of the prefrontal cortex. The nerve growth factor may be directly intracerebrally administered in one dose or in a series of doses to effectively kill or suppress the activity of the subplate cells of the prefrontal cortex. Once the subplate cells are substantially killed or their activity is sufficiently suppressed, the animal is allowed to mature past puberty at which time the animal develops neuropathological and behavioral features of schizophrenia.

According to another aspect of the present invention, there is provided an animal model for schizophrenia, the animal exhibiting neuropathological and behavioral features of human schizophrenia.

According to another aspect of the present invention is a post-natal animal substantially devoid of subplate cells in the developing prefrontal cerebral cortex. In embodiments of the invention, the animal is about 3-4 days post-natal. In other embodiments, such as in primates, the animal is pre-natal (fetal).

According to still another aspect of the present invention is an animal exhibiting neuropathological and behavioral features consistent with human schizophrenia, said animal having the normal development of the prefrontal cortex modified by the premature elimination of the subplate cells during pre-natal or early postnatal life.

According to another aspect of the present invention is an animal model for schizophrenia, wherein said animal has had subplate cells in the developing cerebral cortex substantially eliminated during a critical period when thalamic and dopaminergic fibers begin to invade the developing prefrontal cortex until the subplate cells in the developing prefrontal cerebral cortex undergo natural death, such animals exhibiting neuropathological and behavioral features of human schizophrenia upon maturation of the animal. In an embodiment, this critical period is the neonatal period for animals such as rats and mice and in another embodiment this critical period is the fetal period for animals such as monkeys.

According to another aspect of the present invention is an animal model for schizophrenia, the animal exhibiting one or more of the following:
- enhanced subcortical dopamine responsivity manifested after puberty;
- diminished GABA transporter-1 immunoreactive synapses in the prefrontal cortex;
- altered laminar distribution as well as loss of GABAergic terminals in the prefrontal cortex;
- decreased density of dopamine fibers in this lower layers of the prefrontal cortex; and
- moderately enlarged lateral and third ventricles.

According to yet another aspect of the present invention, is a method for making an animal model of schizophrenia, the method comprising:
- substantially eliminating or suppressing the activity of subplate cells in the developing cerebral cortex during a critical period of said animal, wherein said critical period is the time when thalamic and dopaminergic fibers begin to invade the developing prefrontal cortex until subplate cells of the prefrontal cerebral cortex under go natural death; and
- allowing the animal to mature past puberty.

This critical period for an animal is typically during the neonatal or fetal period.

According to yet another aspect of the invention, is a method for making an animal model of schizophrenia, the method comprising:
- administering an agent to subplate cells in the developing prefrontal cortex of a neonatal or fetal animal wherein said agent substantially kills or suppresses the function of said subplate cells; and
- allowing the animal to mature past puberty.

According to another aspect of the invention, is a method for making an animal model of schizophrenia, the method comprising:
- administering a substance systemically to an animal in order to cause a substantial loss or dysfunction of the subplate cells of the developing prefrontal cortex, and
- allowing the animal to mature past puberty.

According to still another aspect of the invention is a method of testing the efficiency of a therapeutic agent for treating schizophrenia, the method comprising;
- evaluating schizophrenic symptoms of a post-pubertal animal having subplate cells in the developing prefrontal cortex eliminated during a critical period of the animal when thalamic and dopaminergic fiber begin to invade the developing prefrontal cortex until subplate cells of the prefrontal cerebral cortex under go natural death;
- contacting said animal with a therapeutic agent; and
- re-evaluating the symptoms of said animal, wherein prevention, delayed onset, reduction of one or more of the symptoms or a modification of the progress of disease of said animal indicating the therapeutic agent is efficacious for treating schizophrenia.

According to yet another aspect of the present invention is a post-natal or fetal animal substantially devoid of subplate cells in the developing prefrontal cerebral cortex, via the apoptosis of said cells by the intracerebral injection of an agent or administration of an agent or agents by other routes that promotes said apoptosis.

Other features and advantages of the present invention will become apparent from the following detailed description. It should be understood, however, that the detailed description and the specific examples while indicating embodiments of the invention are given by way of illustration only, since various changes and modifications within the spirit and scope of the invention will become apparent to those skilled in the art from said detailed description.

BRIEF DESCRIPTION OF THE DRAWINGS

The present invention will become more fully understood from the detailed description given herein and from the accompanying drawings, which are given by way of illustration only and do not limit the intended scope of the invention.

DETAILED DESCRIPTION OF THE PREFERRED EMBODIMENTS

Figure 1:
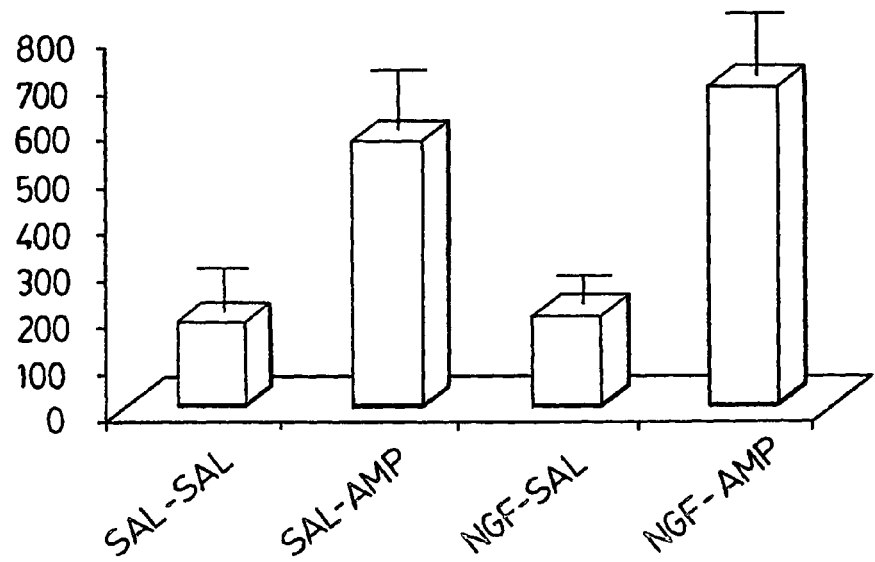
FIG. 1 is a histogram showing the total duration of sniffing behavior at 5 weeks (in seconds per 1 hour) in control (neonatally saline injected) or experimental (neonatally nerve growth factor injected) animals when challenged with an injection of saline or d-amphetamine. The sniffing represents dopamine activity in the striatum. Amphetamine injection increases sniffing in both groups of animals as expected. At 5 weeks, no differences are seen between control and experimental animals. [n=30].
Figure 2:
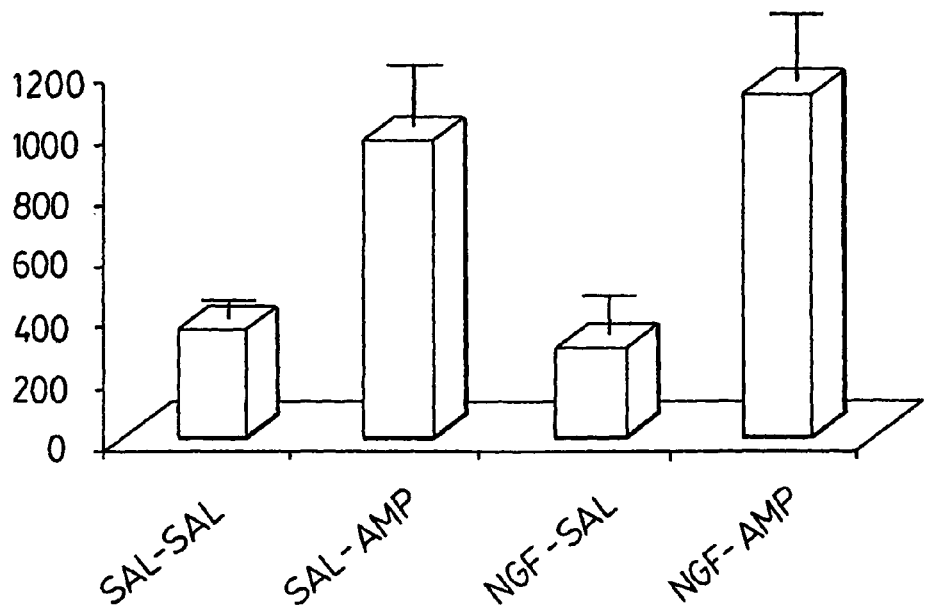
FIG. 2 is a histogram showing the total duration of sniffing behavior at 10 weeks (in seconds per 1 hour) in control (neonatally saline injected) or experimental (neonatally nerve growth factor injected) animals when challenged with an injection of saline or d-amphetamine. Amphetamine injection increases sniffing in both groups of animals. At 10 weeks, no differences are seen between control and experimental animals indicating striatal dopaminergic activity is comparable [n=36].
Figure 3:
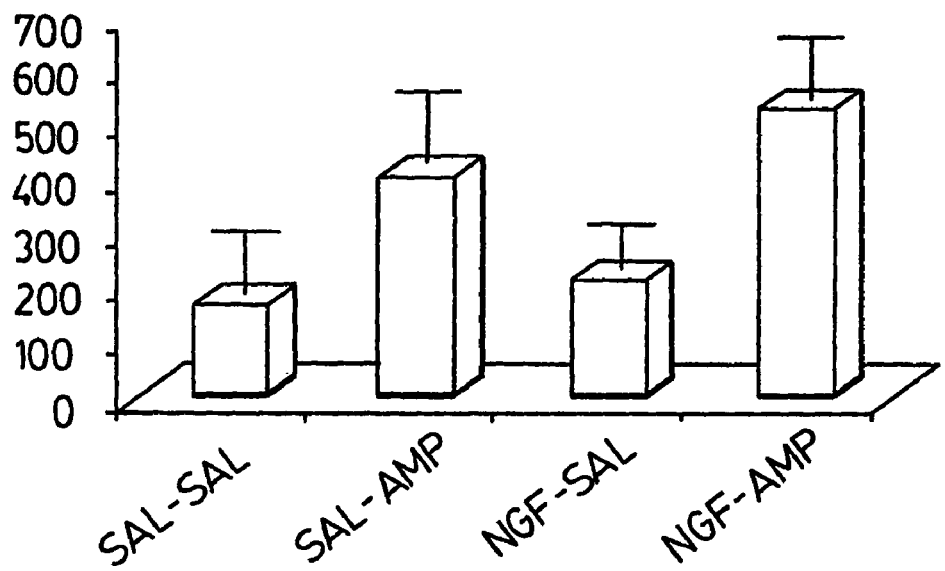
FIG. 3 is a histogram showing the total duration of locomotor behavior at 5 weeks (in seconds per 1 hour) in control (neonatally saline injected) or experimental (neonatally nerve growth factor injected) animals when challenged with an injection of saline or d-amphetamine. The initiation of locomotion is associated with enhanced dopamine activity in the nucleus accumbens. Amphetamine injection increases the total duration of locomotion in both groups of animals as expected. At 5 weeks, no differences in the total duration of locomotion are seen between control and experimental animals, [n=30].
Figure 4:
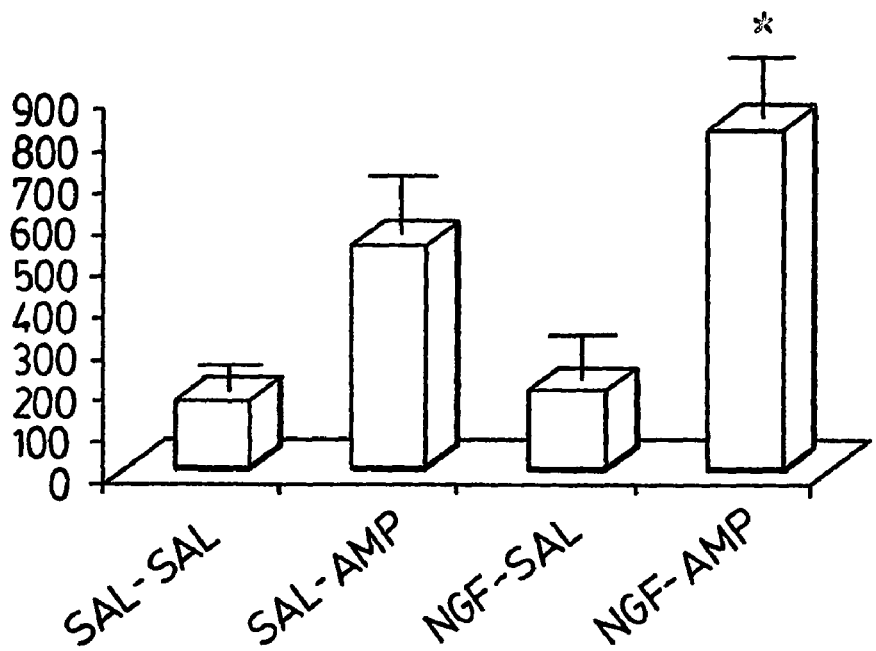
FIG. 4 is a histogram showing the total duration of locomotor behavior at 10 weeks (in seconds per 1 hour) in control (neonatally saline injected) or experimental (neonatally nerve growth factor injected) animals when challenged with an injection of saline or d-amphetamine, Results show that at 10 weeks, d-amphetamine induces a significantly increased locomotor behavior in experimental animals indicating an increased dopaminergic activity in the nucleus accumbens. [n=36].
Figure 5:
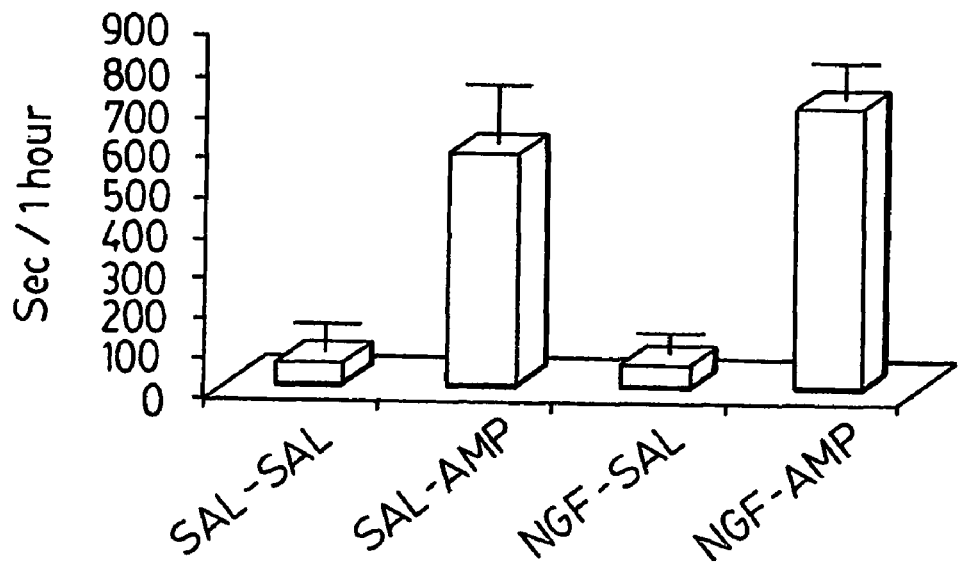
FIG. 5 is a histogram showing the total duration of rearing behavior at 5 weeks (in seconds per 1 hour) in control (neonatally saline injected) or experimental (neonatally nerve growth factor injected) animals when challenged with an injection of saline or d-amphetamine. Rearing is associated with enhanced dopamine activity in the nucleus accumbens. Results show that at 5 weeks, no differences are seen between control and experimental animals. [n=30].
Figure 6:
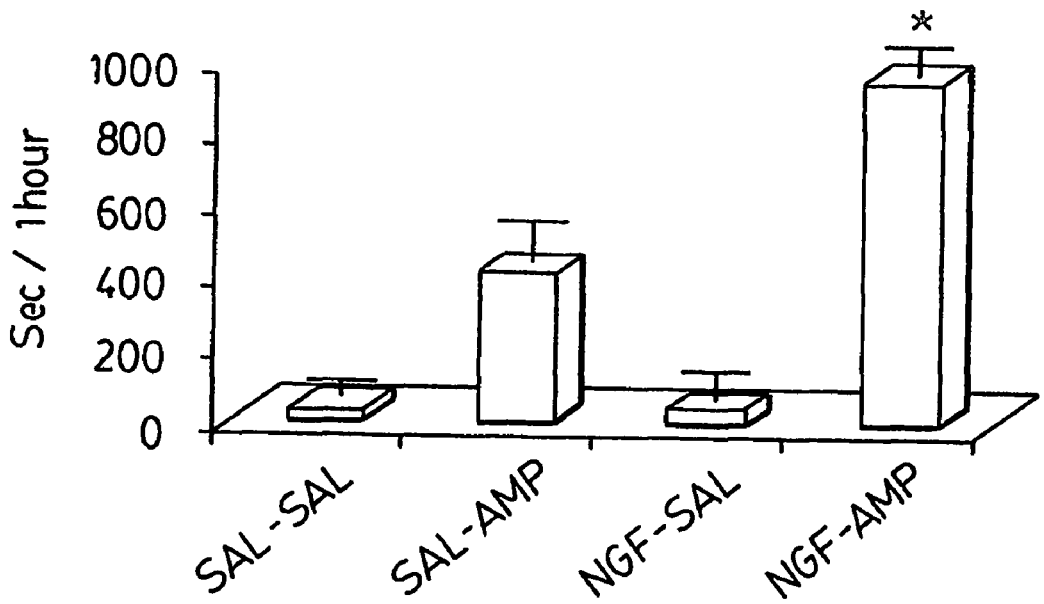
FIG. 6 is a histogram showing the total duration of rearing behavior at 10 weeks (in seconds per 1 hour) in control (neonatally saline injected) or experimental (neonatally nerve growth factor injected) animals when challenged with an injection of saline or d-amphetamine. At 10 weeks, d-amphetamine induces a significantly increased rearing in experimental animals indicating an increased dopaminergic activity in the nucleus accumbens. [n=36].
Figure 7:
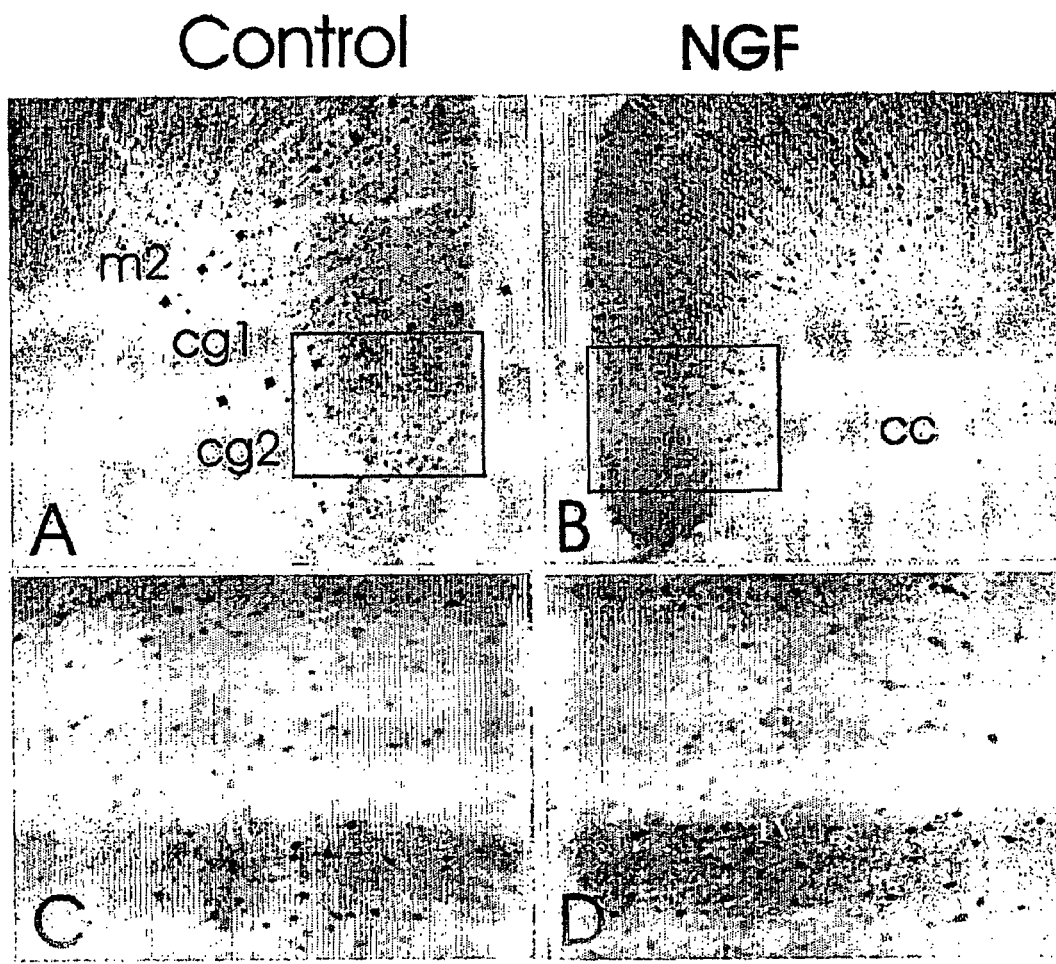
FIGS. 7(A), (B) (C) and (D) are photomicrographs showing parvalbumin immunoreactivity in the prefrontal cortex of an adult control rat (A) and an adult rat received neonatal injections of nerve growth factor (B). Parvalbumin labels a subpopulation of GABAergic neurons and terminals in rat cortex. FIGS. (C) and (D) show magnified view of boxes outlined in (A) and (B), respectively. The experimental animals show altered laminar distribution of parvalbumin immunoreactive terminals. However, the neuronal number is comparable between control and NGF-treated animals (see table).

The present invention provides a novel animal model for humans schizophrenia useful for identifying pharmaceutical compounds for anti-schizophrenic activity. The invention is also a novel in vivo method for the production of an animal model for schizophrenia.

The method of the invention is based on the novel demonstration that premature elimination of subplate cells in the developing prefrontal cortex in postnatal rats leads to the abnormal layer-specific distribution of dopaminergic fibers within the prefrontal cortex. This is associated with subcortical dopaminergic hyperactivity similar to that seen in schizophrenia.

In the normal brain, dopaminergic fibers are distributed mainly in lower layers of the prefrontal cortex, Dopaminergic-fibers are abnormally distributed within the prefrontal cortex in schizophrenic patients with very low density in the lower layers (Akil, Pierri, Whitehead, Edgar, Mohila, Sampson and Lewis, American Journal of Psychiatry 1999, 156: 1580-1589). Recent unpublished work by the inventor indicated that eliminating dopaminergic fibers from the lower layers of the prefrontal cortex in adult rats by intracerebral stereotaxic injections of dopamine-specific neurotoxin, 6-hydroxydopamine, resulted in markedly enhanced subcortical dopaminergic activity to systemic injections of amphetamine. Based on this work the inventor believed that abnormal laminar distribution of dopaminergic fibers in the prefrontal cortex may be responsible for the enhanced dopaminergic activity seen in schizophrenia. While abnormal distribution of dopaminergic fibers has been described in the prefrontal cortex in schizophrenic brains (Akil, Pierri, Whitehead, Edgar, Mohila, Sampson and Lewis, American Journal of Psychiatry 1999, 156:1580-1589), this has never implicated in the manifestation of dopaminergic hyperactivity.

Subplate cells are known to play a role in proper targeting of thalamic fibers within the developing visual cortex in cats and ferrets (Allendoserfer and Shartz, Annual Review of Neuroscience 1994, 17:185-218). Ablation of subplate cells prior to invasion of thalamic fibers into the developing cortical plate results in the abnormal distribution of thalamic fibers in the visual cortex (Ghosh, Ciba Foundation Symposium 1995, 193: 150-172). The role that subplate cells may play in thalamic fiber invasion of the prefrontal cortex is unknown. Moreover, an association between subplate cells and dopaminergic fibers has never been described.

The subplate layer consists of a transient population of cells accumulated underneath the developing cerebral cortex. In humans, subplate cells are generated during 7-9 weeks of gestation and stay until the $35^{th}$-$37^{th}$ week of gestation (Super, Soriano and Uylings, Brain Research Reviews 1998, 27:40-64). It has been shown that incoming thalamocortical fibers make synaptic contacts with subplate cells and literally wait for a considerable length of time within the subplate layer prior to invading the overlying cerebral cortex (Allendoerfer and Shartz, Annual Review of Neuroscience 1994, 17:185-218). This interaction is thought to be necessary for proper target finding of thalamocortical) fibers at least in the visual cortex (Allendoerfer and Shartz, Annual Review of Neuroscience 1994 ,17:185-218). Subsequently, majority of the subplate cells die and the remaining subplate cells become the intestinal neurons of the white matter (Allendoerfer and Shartz, Annual Review of Neuroscience 1994, 17:185-218; Super, Soriano and Uylings, Brain Research Reviews 1998, 27:40-64), The present invention demonstrates that the premature elimination of subplate cells in an animal at a critical time period when thalamic and dopaminergic fibers start invading the developing prefrontal cortex up until the subplate cells under go natural death, results in abnormal distribution of thalamic and dopaminergic fibers within the prefrontal cortex. The critical period is characterized by the expression of the p75 receptor in the absence of the expression of the trkA receptor, This subsequently manifests itself in neuropathological and behavioral features closely resembling human schizophrenia when the animal reaches puberty.

In the present invention, the development of the prefrontal cortex in an animal has been modified by prematurely eliminating the subplate cells, a transient cell layer in the developing prefrontal cortex. Premature elimination of the subplate cells in the developing prefrontal cortex was achieved by a series of intracerebral injections of nerve growth factor administered during the neonatal or fetal period of an animal. Nerve growth factor is not a neurotoxin, but a protein normally found in the brain and essential for the survival and maintenance of certain types of neurons. The method of injection adopted only affects the subplate cells of the prefrontal cortex and does not affect the hippocampus or any other parts of the cerebral cortex. The injected animals grow normally until they become adults, and then they begin to show behavioral changes indicating enhanced subcortical dopamine responsivity, a feature demonstrative of schizophrenia. The animals also show markedly diminished GABA transporter-1 immunoreactive synapses in the prefrontal cortex, altered laminar distribution of GABAergic terminals in the prefrontal cortex, decreased density of dopamine fibers in the lower layers of the prefrontal cortex, and moderately enlarged lateral and third ventricles. These neuropathological changes are frequently observed in postmortem studies in schizophrenic brains.

In the present invention, the applicant eliminated the subplate cells of rats beginning at postnatal day 2 just 4 days prior to the cells natural death. This resulted in abnormal distribution of dopaminergic fibers in the prefrontal cortex in the rat (marked decrease in lower layers), and the development of adult-onset dopaminergic hyperresponsivity along with several neuropathological abnormalities associated with human schizophrenia. In rats, the subplate cells are born at embryonic days 11-12 (rat's gestation period is 21 days). Thalamic and dopaminergic fibers start invading the overlying cortical plate at birth and the majority of subplate cells die by postnatal day 6 (Super, Soriano and Uylings, Brain Research Reviews 1998, 27:40-64).

In the method of the invention, intracerebral injections of nerve growth factor are administered into the developing prefrontal cortex resulting in apoptosis of the subplate cells via a p75 receptor (the nerve growth factor (NGF) receptor) dependent mechanism. This novel method allows for the selective and effective elimination of subplate cells in postnatal rat brain via apoptosis without causing any substantial mechanical, ischemic or inflammatory lesion. Although, studies have indicated abnormal levels and function of neurotrophic factors including nerve growth factor in adult schizophrenic patients (Aloe, lannitelli, Angelucci, Bersani and Fiore, Behavioral Pharmacology 2000, 11: 235-242), a link between the etiology of schizophrenia and nerve growth factor has never been described in addition, the presence of neurotrophic factor predisposing or leading to a brain disease condition has never been considered. Subplate cells express neutrotrophin receptor p75 (Allendoerfer and Shartz, Annual Review of Neuroscience 1994, 17:185-218) and in rats, the subplate cells express neurotrophin receptor p75 postnatally from day 2-6. During the first postnatal period, no trk-A receptors (another type of neurotrophin receptor) are expressed in the developing cerebral cortex in rats. When a cell co-expresses both p75 and trk-A receptors, nerve growth factor normally facilitates survival of that cell (Friedman and Greene, Experimental Cell Research 1999, 253: 131-142). However, in the absence of trk-A receptors, nerve growth factor acting on p75 receptor alone can induce apoptosis or cell death (Frade, Rodriguez-Tebar and Barde, Nature 1996, 383: 166-168). Although nerve growth factor induced p75 receptor mediated apoptosis has been described in certain cell types, it has never been demonstrated in neurons in vivo, nor has such apoptosis been linked to the development of schizophrenia The following is involved in the production of the animal schizophrenia model of the invention.

(1) Killing or Suppressing the Subplate Cells in the Developing Cerebral Cortex.

This is done by introducing a suitable agent that specifically targets and substantially kills or suppresses the function of the subplate cells. Any agent that can initiate the death of these cells or substantially suppress their function without substantially affecting surrounding tissues is encompassed by the present invention. Suitable agents for use in the present invention include but are not limited to nerve growth factor and functional analogues thereof as well as synthetic peptide mimetics, small molecules, other organic and inorganic compounds, agonists that interact specifically with the p75 neurotrophin receptor or its signaling pathways leading to the induction of apoptosis of the subplate cells and mixtures thereof. The present invention also includes compounds that may selectively affect subplate cell viability or function in the developing cerebral cortex via non p75 receptor dependent mechanisms. One of skill in the art can readily determine whether an agent binds and thus interacts with the p75 neurotrophin receptor of subplate cells using assays known in the art. The preferred agent for use in the present invention is nerve growth factor.

Also within the scope of the present invention is the use of pro-nerve growth factor and its analogues as the agent to facilitate the death or suppression of subplate cells. Pro-nerve growth factor that has increased increased affinity (>1000 fold) for p76 receptors (Roux, P. P. and Baker, P. A. (2002), Progress in Neurobiology 67:203-233; Lee, F. S., Kim, A. H., Khursigara, G. and Chao, M. V. (2001), Current Opinion in Neurobiology 11:281-286.

The nerve growth factor (NGF) for use in the invention can be naturally isolated or recombinantly produced human NGF (hNGF) (or other mammalian NGF) that can be administered as the pure or substantially pure compound. As NGF is soluble, it can be provided dissolved in a suitable vehicle and delivered directly to the developing prefrontal cerebral cortex. Methods for making recombinant hNGF are disclosed for example in U.S. Pat. No. 5,082,774 (the contents of which are disclosed herein in its entirety). The nucleotide sequence encoding hNGF is disclosed in U.S. Pat. No. 5,288,622 and described in Johnson, D., et al., Cell, 47:545-554 (1986) (the contents of which is incorporated herein by reference in its entirety). NGF variants that may also be used in the present invention are disclosed for example in U.S. Pat. Nos. 6,365,373 and 6,333,310 (the disclosures of which are herein incorporated by reference in their entirety).

"Functionally equivalent variants" or "analogues" of nerve growth factor includes peptides with partial sequence homology, peptides having one or more specific conservative and/or non-conservative amino acid changes, peptide conjugates, chimeric proteins, fusion proteins and peptide encoding nucleic acids. The functionally equivalent variants maintain the biological activity of the native peptide. One skilled in the art would readily be able to determine what functionally equivalent variants or analogues of nerve growth factor may encompass.

In terms of "functional analogues", it is well understood by those skilled in the art, that inherent in the definition of a biologically functional peptide analogue is the concept that there is a limit to the number of changes that may be made within a defined portion of the molecule and still result in a molecule with an acceptable level of equivalent biological activity. A plurality of distinct peptides/proteins with different substitutions may easily be made and used in accordance with the invention. It is also understood that certain residues are particularly important to the biological or structural properties of a protein or peptide such as residues in the receptor recognition region, such residues of which may not generally be exchanged.

Functional analogues can be generated by conservative or non-conservative amino acid substitutions. Amino acid substitutions are generally based on the relative similarity of the amino acid side-chain substituents, for example, their hydrophobicity, hydrophilicity, charge, size and the like. Thus, within the scope of the invention, conservative amino acid changes means, an amino acid change at a particular position which is of the same type as originally present; i.e. a hydrophobic amino acid exchanged for a hydrophobic amino acid, a basic amino acid for a basic amino acid, etc. Examples of conservative substitutions include the substitution of one polar (hydrophobic) residue such as isoleucine, valine, leucine or methionine for another, the substitution of one polar (hydrophilic) residue for another such as between arginine and lysine, between glutamine and asparagine, between glycine and serine, the substitution of one basic residue such as lysine, arginine or histidine for another, or the substitution of one acidic residue, such as aspartic acid or glutamic acid for another, the substitution of a branched chain amino acid, such as isoleucine, leucine, or valine for another, the substitution of one aromatic amino acid, such as phenylalanine, tyrosine or tryptophan for another. Such amino acid changes result in functional analogues in that they do not significantly alter the overall charge and/or configuration of the peptide. Examples of such conservative changes are well-known to the skilled artisan and are within the scope of the present invention. Conservative substitution also includes the use of a chemically derivatized residue in place of a non-derivatized residue provided that the resulting peptide is a biologically functional equivalent to the nerve growth factor protein.

The present invention also contemplates non-peptide analogues of nerve growth factor for use in the invention, e.g. peptide mimetics that provide a stabilized structure or lessened biodegradation. Peptide mimetic analogues can be prepared based on a selected nerve growth factor peptide sequence by replacement of one or more residues by non-peptide moieties. Preferably, the non-peptide moieties permit the peptide to retain its natural conformation, or stabilize a preferred, e.g. bioactive confirmation. Such peptides can be tested in molecular or cell-based binding assays to assess the effect of the substitution(s) on conformation and/or activity. The preparation of non-peptide mimetic analogues from the peptides of the invention can be done, for example, as taught in Nachman et al., *Regul. Pept.* 57: 359-370 (1995).

In one embodiment of the invention the nerve growth factor is administered directly into the subplate cells of the prefrontal cortex. This is preferably done by intracerebral administration. Any direct method of delivering the nerve growth factor to the subplate cells may be encompassed by the present invention. The amount of nerve growth factor is the amount required to substantially kill and substantially suppress the activity of the subplate cells and can be readily determined for a particular animal and confirmed using standard histological methods (for example immunocytochemistry and in situ hybridization) which can identify cells undergoing apoptosis using standard apoptosis markers such as but not limited to caspase III. The nerve growth factor may be administered in one dose or alternatively, in a series of doses. As a single dose, the nerve growth factor may be provided in a dose and manner to provide for an extended release. The amount of nerve growth factor required in the method of the invention is such that to cause a substantial number of the subplate cells to undergo apoptosis, This may be about at least 25% to 30% of the subplate cells of the developing cerebral cortex leading to the manifestation of neuropathological and behavioral features of human schizophrenia at maturity of the animal.

Figure 9:
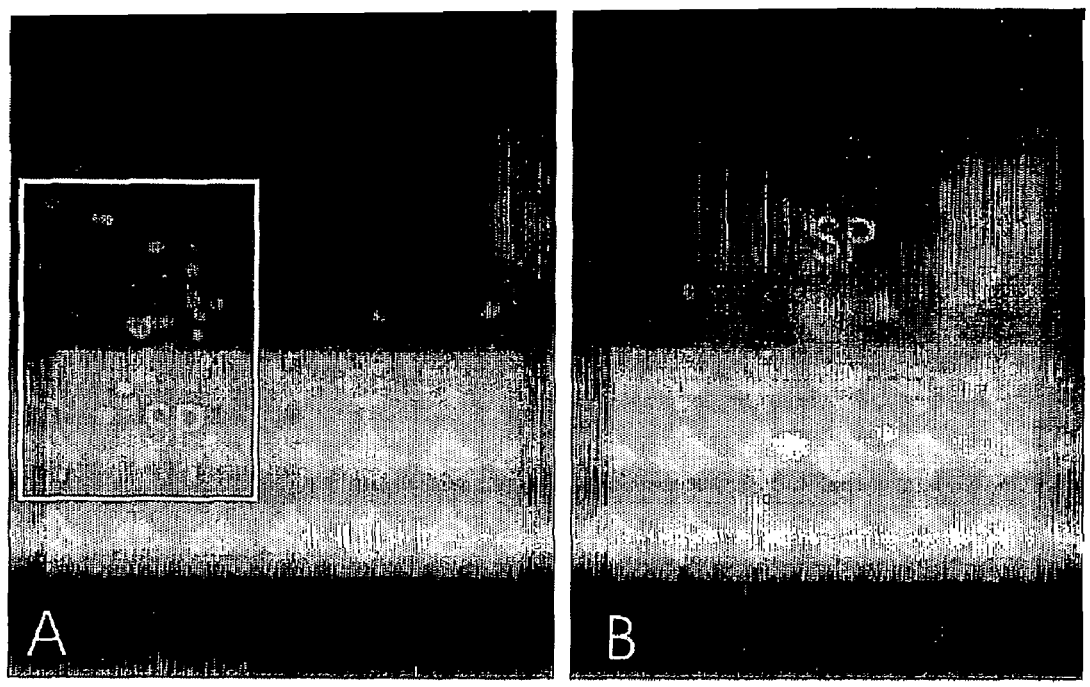
FIGS. 9(A) and (B) are photomicrographs showing immunoreactivity of activated caspase-3 in subplate cells (SP) in the prefrontal cortex of a six day-old rat pup that received intracerebral daily injections of nerve growth factor on postnatal days 2, 3 and 4. Area In (A) is magnified in (B). Activation of caspase-3 indicates that these cells are undergoing apoptosis.

The nerve growth factor must be administered during a "critical period" which is defined as the time period when thalamic and dopaminergic fibers begin to invade the developing prefrontal cortex. This critical period lasts until the subplate cells of the developing prefrontal cerebral cortex undergo natural death. During this critical period the subplate cells express the p75 receptor but not the trkA receptor. The critical period for rats and mice falls during the first week of neonatal period and in monkeys falls during the fetal period. Specifically, for rats and mice this period falls on about days 3-4 after birth. FIGS. 9A and 9B show that postnatal injections of NGF induces apoptosis of the subplate cells, in monkeys the critical period occurs during the fetal period and is readily determined by one of skill in the art based on the developmental pattern of thalamocortical and dopaminergic fibers within the developing prefrontal cortex and the presence of p75 expression by the subplate cells. Therefore, the present invention is not limited to only rats, mice and monkey animal schizophrenia models, but rather any animal so long as the critical period is first determined. The method of the invention is applicable for the production of animal models for schizophrenia in variety of species of animals. In particular, the creation of a non-human primate model of schizophrenia is desirable for more elaborate behavioral and cognitive testing.

(2) Raising the Animals Until they Reach Puberty in Standard Living Conditions.

(3) Objectively Measuring the Animals Behavior to Elicit Dopaminergic Hyperresponsivity in the Brain Once Animals Have Reached Puberty.

Behavioral testing may include those tests known to those of skill in the art and as described herein in example 2. Such tests assess vertical and horizontal locomotor activity in a familiar and novel environment after challenging them with a pharmaceutical compound such as amphetamine that stimulates dopamine activity in the brain, after subjecting animals to stressful situation, or after restraining them. Once the behavioral abnormalities have been established, those animals exhibiting the abnormalities characteristic of schizophrenia may be used in screening pharmaceutical compounds for their potential antipsychotic property, cognitive enhancement, and their potential ability to reverse or ameliorate the high dopaminergic activity in the brain. In addition, these animals may be used in studies to determine molecular mechanisms of manifestation of schizophrenic symptoms, and to study the natural progression of pathophysiology and effects of treatment.

In accordance with the method of the invention, two daily injections of nerve growth factor (250 ng/μl/site) into the developing cerebral cortex at postnatal days 3 and 4 in rats specifically induced apoptosis of subplate neurons and eliminated them prematurely (FIGS. 9A, 9B). A control group of rat pups received similar saline injections and did not show any effects on the viability of subplate neurons. Both experimental and control groups of rats were raised under standard conditions, and they showed comparable growth and behavioral patterns until 8 weeks of age, After the 8$^{th}$ week, only the experimental animals that received the nerve growth factor started to exhibit a prolonged and enhanced response to changes in the environment, and behaviors indicative of an increased subcortical dopaminergic responsivity to injections of d-amphetamine (FIGS. 1-6). Behaviors typically tested to Identify enhanced dopaminergic responsivity include, but not limited to, stress-induced hyperactivity, dopamimetic drug-induced hyperactivity and stereotypy and abnormal social interaction.

Figure 8:
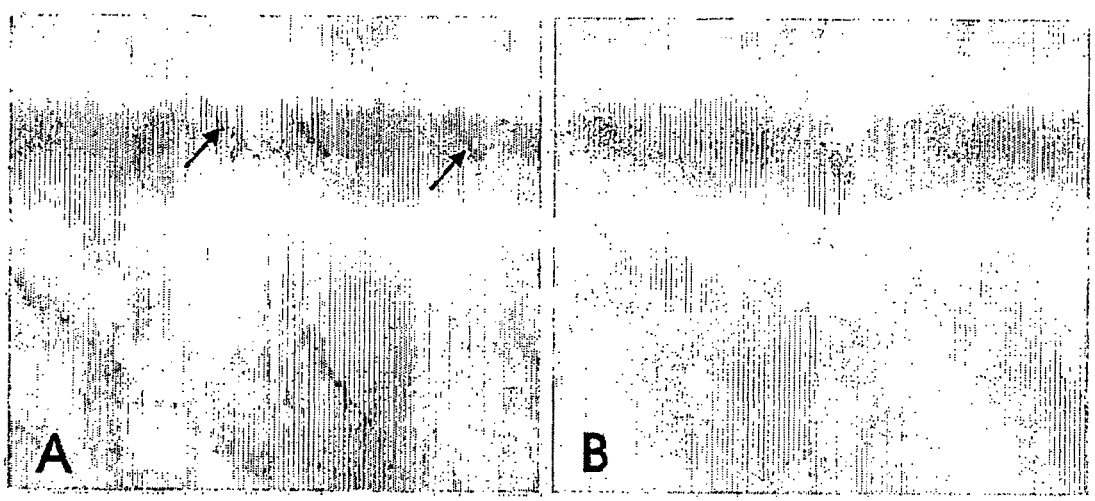
FIGS. 8(A) and (B) are photomicrographs showing GABA transporter-1 immunoreactivity in the prefrontal cortex of an adult control rat (A) and an adult rat received neonatal injections of nerve growth factor (B). GABA transporter-1 immunoreactive synapses (arrows) are fewer in animals that received neonatal nerve growth factor injections.
Figure 10:
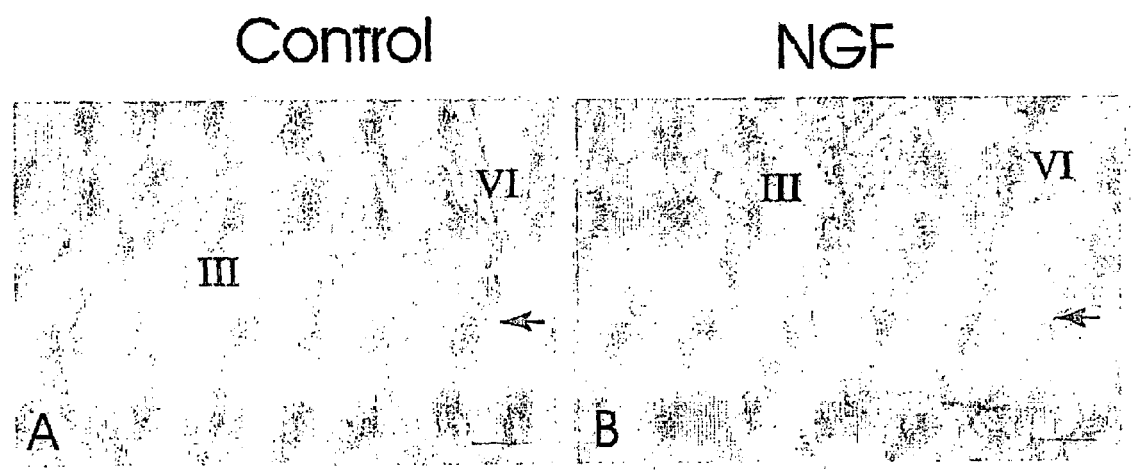
FIGS. 10(A) and (B) are photomicrographs showing tyrosine hydroxylase immunoreactivity in the prefrontal core)t of an adult control rat (A) and an adult rat received neonatal injections of nerve growth factor (B). Tyrosine hydroxylase is the rate-limiting enzyme of dopamine synthesis and used here as a marker. The density of tyrosine hydroxylase labeled fibers is considerably decreased in lower layers (layer VI) of the prefrontal cortex in animals that received neonatal nerve growth factor injections (B) in comparison to control animals (A)
Figure 11:
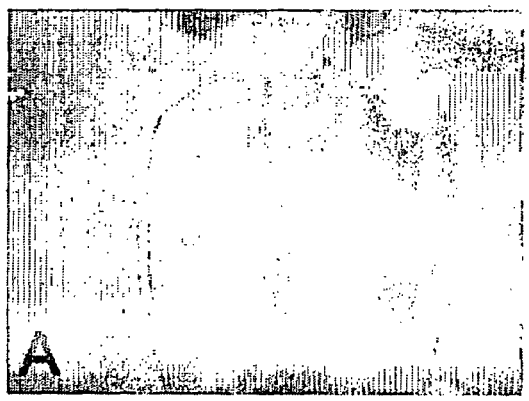
FIG. 11 is a photomicrograph showing coronal sections through the lateral ventricles (LV) of a control rat sacrificed at 6 months of age (A) and a rat that received neonatal injections of NGF sacrificed at 6 months of age (B). Note that the volume of lateral ventricles have increased considerably in rat that received neonatal injections of NGF.
Figure 11:
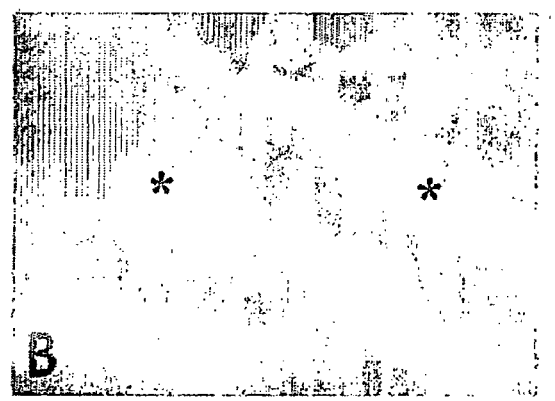

Histological examination of brains of these animals showed apparently normal gross structure throughout the brain. Only microscopic abnormalities were seen in the organization of synapses in the prefrontal cortex (FIG. 10A, 10B), particularly in the pattern of distribution of GABAergic terminals. Nerve growth factor treated animals also showed decreased dopaminergic fibers in lower layers of the prefrontal cortex. The number of GABA transporter-1-containing synapses of a particular type of cortical interneurons was markedly diminished in NGF treated animals (FIG. 8A, 8B), a feature consistently shown in postmortem brains of schizophrenia (Volk, Austin, Pierri, Sampson and Lewis, American Journal of Psychiatry 2001, 158: 256-265; Woo, Whitehead, Melchitzky and Lewis, Proceedings of the National Academy of Science USA. 1998, 95: 5341-5346). In addition, nerve growth factor treated animals showed relatively larger lateral and third ventricular size in comparison to control animals. Therefore, daily injections of nerve growth factor into the developing prefrontal cortex in postnatal day 2, 3 and 4 in rat pups resulted in adult-onset behavioral abnormalities and cortical and ventricular abnormalities similar to that seen in schizophrenic patients. In these animals, the remainder of brain areas are apparently normal therefore allows standard behavioral and cognitive testing.

To summarize, the present invention has for the first time demonstrated a link between abnormal dopaminergic fiber distribution in the prefrontal cortex and subcortical dopaminergic hyperresponsivity; the association between prefrontal cortical subplate and dopaminergic fiber distribution within the prefrontal cortex; the critical time to eliminate prefrontal cortical subplate cells; and inducing apoptosis of subplate cells by intracerebral injections of nerve growth factor, The invention provides novel methods of producing animal models (both rodent and non-human primate) showing neuropathological and behavioral features of schizophrenia. Therefore, this invention provides a unique animal model of schizophrenia showing both behavioral and neuropathological features in addition, no brain area in this model shows gross structural damage, a feature seen in schizophrenic brains.

The animal model of schizophrenia produced by the method of the invention may be used in screening pharmaceutical agents for their potential beneficial effect in the treatment of schizophrenic symptoms. In addition, since there is no gross structural damage to the hippocampus, amygdala or the thalamus in this animal model, this model could be used in tests for memory and cognitive function. Therefore, the present animal model can be used in screening pharmaceutical compounds for their potential effects in cognitive functioning and memory impairment associated with schizophrenia. Currently, no suitable schizophrenia animal models are available for cognitive testing.

This invention provides behavioral, immunohistochemical and neuropathological profiles in an animal model that are seen in human schizophrenia. The present animal model mimics the condition and progression of the condition. Using this in vivo model, one can screen and evaluate various potential therapies or other modalities for their effectiveness in treating or alleviating schizophrenic symptoms and evaluate any potential prophylactics in the prevention of schizophrenic symptoms. Since the model is an in vivo model system it replicates, or is analogous to, the human clinical condition and therefore, useful in eliciting clinical responses to potential antipsychotic and cognitive medications. Further, the model provides a means to evaluate the effect of dosages, routes of administration, schedules, delivery systems, drug sensitivities, side effects and therapeutic efficacy for any potential pharmaceutical compounds in the effective treatment of schizophrenia.

The above disclosure generally describes the present invention. A more complete understanding can be obtained by reference to the following specific Examples. These Examples are described solely for purposes of illustration and are not intended to limit the scope of the invention. Changes in form and substitution of equivalents are contemplated as circumstances may suggest or render expedient. Although specific terms have been employed herein, such terms are intended in a descriptive sense and not for purposes of limitation.

EXAMPLES

The examples are described for the purposes of illustration and are not intended to limit the scope of the invention.

Methods of synthetic chemistry, protein and peptide biochemistry, molecular biology, neuroscience, behavioral science and pharmacology referred to but not explicitly described in this disclosure and examples are reported in the scientific literature and are well known to those skilled in the art.

Neonatal Injections

Neonatal rat pups received daily injections of nerve growth factor into the developing prefrontal cortex at 2, 3 and 4 days of age (similarly other animals such as mice or monkeys can be injected at the appropriate neonatal or fetal period of prefrontal cortical development characterized by the expression of p75 receptor in subplate cells). Scalp of rat pups were sprayed with a topical anesthesia, and 1 µl of nerve growth factor (250 nM/µl in saline, human recombinant Nerve growth factor, Cedarlane Laboratories) was pressure injected with a 30 gauges needle into the developing prefrontal cortex on each side. Injections were made 1.5 mm in front of the bregma which is visible through the scalp, 0.5 mm lateral to the midline and 1.5 mm deep to the scalp surface. Injections were made slowly over 10 sec and the needle was left in situ for an additional 30 sec. Pups were kept separated from their mother for approximately 20 min during injecttion sessions. During this time they were kept warm. Control rat pups received exactly similar treatment but injected with saline. Experimental and control rats were marked with an ear punch on the right and left ears, respectively. After injection session pups were returned to their mother and allowed to grow under standard conditions.

Behavioral Testing

Animals at 5 or 10 weeks of age were habituated to the testing area for three hours each on 2 consecutive days. On the 3rd day, animals were habituated for an hour and then injected with saline (0.2 ml, l.p.) and their behaviors were monitored visually for an hour. They were then injected with d-amphetamine (5 mg/kg, l.p.) and their behaviors were monitored for an additional one-hour. An examiner who was blind to the animal groups performed testing. Several behavioral measures including locomotion, rearing (vertical activity), sniffing and grooming were monitored. Different cohorts of animals were used for testing at 5 and 10 weeks. For stress response, animals were submerged in water at room temperature for 5 min in a large container, then they were placed in a plexiglass box and their behaviors (similar to those described above) were visually monitored, For novelty induced stress response, animals were subjected to novel environment or object and their motor behaviors were monitored. Behavioral data was analyzed using standard statistical methods (Rajakumar, Laurier, Niznik and Stoessi, Synapse 1997, 26: 199-208).

Histological Methods

Both neonatally nerve growth factor or saline injected rats were anesthetized with an intraperitoneal injection of sodium pentobarbital (Somnatol, 40 mg/kg) at 5 weeks or 10 weeks of age and perfused transcardially with a solution containing 4% freshly depolymerized paraformaldehyde in 0.1 M phosphate buffer at pH 7.4. Brains were removed, cryoprotected in 18% buffered-sucrose for 24 hours at 4° C., and sectioned in a freezing microtome 40 μm thick sections were processed for Nissl staining and immunohistochemistry as described previously (Rajakumar, Elisevich and Flumerfelt, Journal of Comparative Neurology 1994, 350:324-336).

REFERENCES

Akil, M., Pierri, J. N., Whitehead, R. E. Edgar, C. L., Mohila, C., Sampson, A. R. and Lewis, D. A. (1999) Lamina-specific alterations in the dopamine innervation of the prefrontal cortex in schizophrenic subjects. American Journal of Psychiatry 156:1580-1589.

Allendoerfer, K. L. and Shartz, C. J. (1994) The subplate, a transient neocortical structure: Its role in the development of connections between thalamus and cortex. Annual Review of Neuroscience 17: 185-218.

Anderson, S. A., Volk, D. W. and Lewis, D. A. (1996) increased density of microtubule associated protein 2-immunoreactive neurons in the prefrontal white matter of schizophrenic subjects. Schizophrenia Research 18: 111-119.

Aloe, L., Iannitelli, A., Angelucci, F., Bersani, G. and Fiore, M. (2000) Studies in animal models and humans suggesting a role of nerve growth factor in schizophrenia-like disorders. Behavioral Pharmacology 11(3-4): 235-242.

Chua, S. E. and McKenna, P. J. (1995) Schizophrenia—a brain disease? A critical review of structural and functional cerebral abnormality in the disorder. British Journal of Psychiatry 166: 563-582.

Friedman, W. J. and Greene. L. A. (1999) Neurotrophin signalling via Trks and p75. Experimental Cell Research 253: 131-142.

Frade, J. M., Rodriguez-Tebar, A. and Barde, Y. A. (1996) induction of cell death by endogenous nerve growth factor through its p75NTR receptor. Nature 383: 166-168.

Ghosh, A. (1995) Subplate neurons and the patterning of thalamocortical connections. Ciba Foundation Symposium 193: 160-172.

Harrison, P. J. (1999) The neuropathology of schizophrenia—A critical review of the data and their interpretation. Brain 122: 593-624.

Johnson, D., Lanahan, A., Buck, C. R., Sehgal, A., Morgan, C., Mercer, E., Bothwell, M. and Chao, M. (1986) Expression and structure of the human NGF receptor. Cell. 47(4):545-554.

Kokkinidis, L. and Anisman, H. (1980) Amphetamine models of paranoid schizophrenia: an overview and elaboration of animal experimentation. Psychological Bulletin 88: 551-579.

Lee, F. S., Kim, A. H., Khursigara, G. and Chao, M. V. (2001), The uniqueness of being a neutrophin receptor, Current Opinion in Neurobiology 11:281-286.

Lewis D. A. Levitt P. Schizophrenia as a disorder of neurodevelopment. [Review] [118 refs] [Journal Article. Review. Review, Academic] Annual Review of Neuroscience. 25:409-32, 2002.

Lipska, B. K., Jaskiw, G. E. and Weinberger, D. R. (1993) Postpubertal emergence of hyperresponsiveness to stress and to amphetamine after neonatal excitotoxic hippocampal damage: a potential animal model of schizophrenia. Neuropsychopharmacology 9:67-75.

lipska, B. K., Halim, N. D., Segal, P. N. and Weinberger, D. R. (2002) Effects of reversible inactivation of the neonatal ventral hippocampus on behavior in the adult rat. Journal of Neuroscience 22(7): 2835-2842.

Marenco, S. and Weinberger, D. R. (2000) The neurodevelopmental hypothesis of schizophrenia: following a trail of evidence from cradle to grave. Developmental Psychopathology 12(3); 501-527.

Nachman, R. J., Roberts, V. A., Holman, G. M. and Beler, R. C. (1995) Pseudodipeptide analogs of the pyrokinin/PBAN (FXPRLa) insect neuropeptide family containing carbocyclic Pro-mimetic conformational components. Regulatory Peptides. 57(3):359-370.

Rajakumar, N., Laurier, L., Nlznik, H. B. and Stoessi, A. J. (1997) Effects of intrastriatal infusion of D2 receptor antisense oligonucleotide on apomorphine-induced behaviors in the rat. Synapse 26(3): 199-208.

Rajakumar, N., Elisevich, K. and Flumerfelt, B. A. (1994) Parvalbumin-containing GABAergic neurons in the basal ganglia output system of the rat. Journal of Comparative Neurology 350(2): 324-330.

Roux, P. P. and Baker, P. A. (2002), Neurotrophin signalling through the p75 neurotrophin receptor, Progress in Neurobiology 67:203-233.

Super, H., Sotiano, E. and Uylings, H. B. M. (1998) The functions of the preplate in development and evolution of the neocortex and hippocampus. Brain Research Reviews 27:40-64.

Uehara, T., Tanii, Y., Sumiyoshi, T. and Kurachi, M. (2000) Neonatal lesions of the left entorhinal cortex affect dopamine metabolism in the rat brain. Brain Research 860: 77-66.

Volk, D., Austin, M., Plerri, J., Sampson, A. and Lewis, D. (2001) GABA transporter-1 mRNA in the prefrontal cortex in schizophrenia: decreased expression in a subset of neurons. American Journal of Psychiatry 158(2), 256-265.

Woo, T. U., Whitehead, R. E., Melchitzky, D. S. and Lewis, D. A. (1998) A subclass of prefrontal gamma-aminobutyric acid axon terminals are selectively altered in schizophrenia. Proceedings of the National Academy of Science USA, 95(9): 5341-5346.

The invention claimed is:

1. A non-human animal model of schizophrenia, wherein said animal has had the subplate cells in die developing cerebral cortex prematurely eliminated in vivo by direct administration of nerve growth factor to the subplate cells of the prefrontal cortex during a critical period when thalamic and dopaminergic fibers begin to invade the developing prefrontal cortex until the time the subplate cells under go natural death, wherein said animal exhibits neuropathological and behavioral features of schizophrenia upon maturation and has intact thalamic, hippocampal, cortical and subcortical circuits as seen in human schizophrenic patients.

2. The animal model of claim 1, wherein said subplate cells during said critical period substantially express the p75 receptor and substantially do not express the trkA receptor.

3. The animal model of claim 1, wherein the administration of said nerve growth factor kills or suppresses the function of the subplate cells.

4. The animal model of claim 3, wherein the administration of said nerve growth factor promotes apoptosis of the subplate cells.

5. The animal model of claim 1, wherein administration of said nerve growth factor is done by single or multiple intracerebral injection.

6. The animal model of claim 1, wherein said animal exhibits one or more of the following characteristics:
enhanced subcortical dopamine responsivity;
diminished GABA transporter-1 immunoreactive synapses in the prefrontal cortex;
altered laminar distribution of GABAergic terminals in the prefrontal cortex;
decreased density of dopamine fibers in the lower layers of the prefrontal cortex; and
moderately enlarged lateral and third ventricles.

7. The animal model of claim 6, wherein said animal is selected from the group consisting of rats, mice and monkeys.

8. The animal model of claim 7, wherein said animal is a rat administered intracerebral injections of nerve growth factor at days 2, 3 and/or 4 postnatally to prematurely eliminate said subplate cells.

9. A method for making a non-human animal model of schizophrenia, the method comprising: eliminating or suppressing the activity of subplate cells in the developing cerebral cortex by direct administration of nerve growth factor to the subplate cells of the prefrontal cortex during a critical period of said animal, wherein said critical period is the time when thalamic and dopaminergic fibers begin to invade the developing prefrontal cortex until subplate cells of the prefrontal cerebral cortex die; and allowing the animal to mature past puberty to exhibit neuropathological and behavioral features of schizophrenia with intact thalamic, hippocampal, cortical and subcortical circuits as seen in human schizophrenic patients.

10. The method of claim 9, wherein said eliminating or suppressing the activity of subplate cells is resulted from apoptosis of said cells.

11. The method of claim 10, wherein said nerve growth factor is administered by one or more intracerebral injections to said cerebral cortex.

12. The method of claim 9, wherein said subplate cells are characterized by the expression of p75 receptor and substantially no expression of a trkA receptor.

13. The method of claim 9, wherein said animal is selected from the group consisting of rat, mouse and monkey.

14. The method of claim 13, wherein said animal exhibits one or more of the following characteristics;
enhanced subcortical dopamine responsivity;
diminished GABA transporter-1 immunoreactive synapases in the prefrontal cortex; and
altered laminar distribution of GABAergic terminals in the prefrontal cortex;
decreased density of dopamine fibers in the lower layers of the prefrontal cortex; and
moderately enlarged lateral and third ventricles.

15. A method of testing the efficiency of a therapeutic agent for treating schizophrenia, the method comprising:
evaluating schizophrenia symptoms of the non-human animal of claim 1, wherein said animal has had the subplate cells in the developing cerebral cortex prematurely eliminated in vivo by direct administration of nerve growth factor to the subplate cells of the prefrontal cortex during a critical period when thalamic and dopaminergic fibers begin to invade the developing prefrontal cortex until the time the subplate cells undergo natural death, wherein said animal exhibits neuropathological and behavioral features of schizophrenia upon maturation and has intact thalamic, hippocampal, cortical and subcortical circuits as seen in human schizophrenic patients, and wherein said symptoms comprise one or more of:
enhanced subcortical dopamine responsivity;
diminished GABA transporter-1 immunoreactive synapascs in the prefrontal cortex; and
altered laminar distribution of GABAergic terminals in the prefrontal cortex;
decreased density of dopamine fibers in the lower layers of the prefrontal cortex;
moderately enlarged lateral and third ventricles;
decreased cognitive function; and
memory impairment;
contacting said animal with a therapeutic agent; and
re-evaluating the symptoms of said animal, wherein reduction of one or more of the symptoms of the progress of disease of said animal indicates that the therapeutic agent is efficacious for treating schizophrenia.

16. The method of claim 15, wherein said subplate cells during said critical period express the p75 receptor and substantially do not express the trkA receptor.

17. The method of claim 16, wherein the administration of said nerve growth factor kills Or suppresses the function of the subplate cells.

18. The method of claim 17, wherein the administration of said nerve growth factor promotes apoptosis of the subplate cells.

19. The method of claim 15, wherein administration of said nerve growth factor is done by single or multiple intracerebral injection.

20. A post-natal or fetal non-human animal substantially devoid of subplate cells in the developing prefrontal cerebral cortex, the apoptosis of said cells by the direct administration of nerve growth factor to the subplate cells of the prefrontal cortex, wherein said animal has intact thalamic, hippocampal, cortical and subcortical circuits as seen in human schizophrenic patients.

21. The animal of claim 1 wherein said animal is post-natal or fetal, said animal exhibiting substantially impaired subplate function in the developing prefrontal cortex following administration of the nerve growth factor.

22. The animal of claim 20, wherein said animal is allowed to mature and exhibits neuropathological and behavioral features of human schizophrenia.

* * * * *